US008937168B2

(12) United States Patent
Evans et al.

(10) Patent No.: US 8,937,168 B2
(45) Date of Patent: Jan. 20, 2015

(54) METHOD OF PRODUCING PURIFIED REBAUDIOSIDE A COMPOSITIONS USING SOLVENT/ANTISOLVENT CRYSTALLIZATION

(75) Inventors: Jeffrey C. Evans, St. Michael, MN (US); John J. Hahn, Maple Grove, MN (US); Allan S. Myerson, Chicago, IL (US); Timothy Oolman, Plymouth, MN (US); Troy A. Rhonemus, Plymouth, MN (US); Kern M. Storo, Burnsville, MN (US); Christopher A. Tyler, Minnetonka, MN (US)

(73) Assignee: Cargill, Incorporated, Wayzata, MN (US)

( * ) Notice: Subject to any disclaimer, the term of this patent is extended or adjusted under 35 U.S.C. 154(b) by 315 days.

(21) Appl. No.: 12/524,134

(22) PCT Filed: Jan. 18, 2008

(86) PCT No.: PCT/US2008/000700
§ 371 (c)(1),
(2), (4) Date: Oct. 22, 2009

(87) PCT Pub. No.: WO2008/091547
PCT Pub. Date: Jul. 31, 2008

(65) Prior Publication Data
US 2010/0099857 A1    Apr. 22, 2010

Related U.S. Application Data

(60) Provisional application No. 60/881,798, filed on Jan. 22, 2007, provisional application No. 61/008,163, filed on Dec. 19, 2007.

(51) Int. Cl.
*C07G 3/00* (2006.01)
*A23L 1/236* (2006.01)
*A23L 2/60* (2006.01)
*C07H 1/08* (2006.01)
*C07H 15/256* (2006.01)

(52) U.S. Cl.
CPC ............... *A23L 1/2366* (2013.01); *A23L 2/60* (2013.01); *C07H 1/08* (2013.01); *C07H 15/256* (2013.01); *A23V 2002/00* (2013.01)
USPC ...................................... 536/18.5

(58) Field of Classification Search
USPC ........................................... 536/18.5
See application file for complete search history.

(56) References Cited

U.S. PATENT DOCUMENTS

| 4,082,858 | A | 4/1978 | Morita et al. |
| 4,361,697 | A | 11/1982 | Dobberstein et al. |
| 4,612,942 | A | 9/1986 | Dobberstein et al. |
| 4,892,938 | A | 1/1990 | Giovanetto |
| 5,112,610 | A | 5/1992 | Kienle |
| 5,962,678 | A * | 10/1999 | Payzant et al. ............... 536/128 |
| 5,972,120 | A | 10/1999 | Kutowy et al. |
| 2003/0138538 | A1 | 7/2003 | Kitazume et al. |
| 2006/0083838 | A1* | 4/2006 | Jackson et al. ............... 426/548 |
| 2006/0134292 | A1 | 6/2006 | Abelyan et al. |
| 2006/0142555 | A1 | 6/2006 | Jonnala et al. |
| 2007/0082103 | A1 | 4/2007 | Magomet et al. |
| 2007/0292582 | A1 | 12/2007 | Prakash et al. |

FOREIGN PATENT DOCUMENTS

| CA | 2185496 | | 3/1998 | |
| CN | 1192447 | A | 9/1998 | |
| CN | 1238341 | A | 12/1999 | |
| CN | 1243835 | | 2/2000 | |
| CN | 1078217 | C | 1/2002 | |
| JP | 52-23100 | | 2/1977 | |
| JP | 52-062300 | | 5/1977 | |
| JP | 55-92400 | | 7/1980 | |
| JP | 56-121453 | | 9/1981 | |
| JP | 56-121454 | | 9/1981 | |
| JP | 56-121455 | | 9/1981 | |
| JP | 56121453 | A * | 9/1981 | ............... C07H 1/08 |
| JP | 57-86264 | | 5/1982 | |
| JP | 62-146599 | | 6/1987 | |
| JP | 63-173531 | | 7/1988 | |
| JP | 2-261359 | | 10/1990 | |
| JP | 06192283 | | 7/1994 | |
| JP | 7-143860 | | 6/1995 | |
| JP | 7-177862 | | 7/1995 | |
| JP | 8-214 | | 1/1996 | |
| JP | 11-243906 | | 9/1999 | |
| JP | 2002-45145 | | 2/2002 | |
| JP | 2002-262822 | | 9/2002 | |
| JP | 2004-344071 | | 12/2004 | |
| KR | 1996-0016568 | B1 | 12/1996 | |
| WO | 00/49895 | | 8/2000 | |
| WO | 03/033097 | | 4/2003 | |
| WO | WO 03/033097 | A * | 4/2003 | ............... B01D 9/00 |
| WO | 2006/038221 | | 4/2006 | |
| WO | 2006/045023 | | 4/2006 | |
| WO | 2006/072921 | | 7/2006 | |

OTHER PUBLICATIONS

Ault, A. Techniques and Experiments for Organic Chemistry, 5th Edn., 1994, p. 47-48.*
Database WPI Week 198145, Thomson Scientific, London GB; AN 1981-82358D; XP002490544, 1 pg.
International Search Report from PCT/US2008/000700, mailed Jul. 31, 2008, 2 pages.

* cited by examiner

*Primary Examiner* — Ganapthy Krishnan (57) ABSTRACT

The invention provides methods of purifying rebaudioside A from a mixture comprising glycosides of the plant *Stevia rebaudiana*. The methods of the invention are useful for preparing highly pure rebaudioside A compositions from crude *Stevia* starting compositions that are typically considerably lower in rebaudioside A concentration. The highly pure rebaudioside A compositions are useful as non-caloric sweeteners in edible or chewable compositions such as food, beverages, medicine, candy, chewing gum, and the like.

45 Claims, 2 Drawing Sheets

METHOD OF PRODUCING PURIFIED REBAUDIOSIDE A COMPOSITIONS USING SOLVENT/ANTISOLVENT CRYSTALLIZATION

CROSS-REFERENCE TO RELATED APPLICATIONS

The present patent Application claims benefit from U.S. Provisional Patent Application having Ser. No. 60/881,798, filed on Jan. 22, 2007, titled METHOD OF PRODUCING PURIFIED REBAUDIOSIDE A COMPOSITIONS USING SOLVENT/ANTISOLVENT CRYSTALLIZATION, and U.S. Provisional Patent Application having Ser. No. 61/008, 163, filed on Dec. 19, 2007, titled METHOD OF PRODUCING PURIFIED REBAUDIOSIDE A COMPOSITIONS USING SOLVENT/ANTISOLVENT CRYSTALLIZATION, wherein the entirety of said provisional patent applications are incorporated herein by reference.

FIELD

The invention relates to the purification of rebaudioside A from crude extracts of the plant *Stevia rebaudiana* using solvent/antisolvent crystallization.

BACKGROUND

The species *Stevia rebaudiana* ("*Stevia*") has been the subject of considerable research and development efforts directed at the purification of certain naturally occurring sweet glycosides of *Stevia* that have potential as non-caloric sweeteners. Sweet glycosides that may be extracted from *Stevia* include the six rebaudiosides (i.e., rebaudioside A to F), stevioside (the predominant glycoside in extracts from wild type *Stevia*), dulcosides, and sterebins.

Rebaudioside A is the sweetest tasting of the glycosides of *Stevia*, having roughly 250-450 times the sweetness of sucrose. Of the glycosides, it is generally agreed that rebaudioside A is the most desirable for use in non-caloric sweeteners because of its favorable sweetness profile, regulatory approvals, customer acceptance, and minimal bitter aftertaste.

Various methods have been reported for the purification of rebaudioside A from crude rebaudioside A containing *Stevia* extracts.

Japanese Publication No. 56121454 reports a method of separating stevioside and rebaudioside A at high purity and yield by crystallization. In the method a mixture of stevioside and rebaudioside A is extracted from the leaves and stalks of *Stevia rebaudiana* Bertoni by conventional process. The extract is dissolved in 0.70% aqueous solution of ethanol and rebaudioside A is selectively crystallized from the solution.

Japanese Patent 63173531 describes a method of extracting sweet glycosides from the *Stevia rebaudiana* plant. The first step of the process is to extract a liquid solution of sweet glycosides from the *Stevia rebaudiana* plant. Secondly, the liquid solution of sweet glycosides is passed through a nonpolar porous resin and is eluted with a water-soluble organic solvent, preferably methanol. Thirdly, the eluted solution is concentrated and dried to give a powdery material. This procedure isolates a mixture of sweet glycosides, but does not isolate a single pure sweet glycoside such as rebaudioside A.

U.S. Patent Application Publication No. 2006/0083838 (Jackson et al.) reports a method of isolating and purifying rebaudioside A from commercially available *Stevia rebaudiana* starting material. The method comprises: (1) an EtOH formulation stage to formulate a selected EtOH solvent, (2) a first reflux stage using the *Stevia* starting material and optionally additional reflux stages using retentate isolated from a refluxed mixture or a stirred wash mixture, (3) optionally, one or more stirred wash stages, and (4) an ethanol purge and drying stage. In embodiments that use lower quality *Stevia* starting material, a second reflux stage is typically added before the stirred wash stage to maximize purity of the rebaudioside A final product. In the reported method, an EtOH formulation stage is conducted in order to formulate a desired reflux solvent for use in the reflux step(s). Typically, the reflux solvent is a mixture of ethanol and water with about 5% to 15% by volume water. The process further includes one or more energy-intensive refluxing steps that are typically conducted at a temperature of about 89° C. to 90° C. for about 1 hour. The method reportedly produces 100% pure, water-soluble rebaudioside A.

U.S. Pat. No. 5,962,678 (Payzant et al.) reports a method of extracting selected sweet glycosides from the *Stevia rebaudiana* plant. In the reported method, sweet glycosides are extracted from the *Stevia* plant and are processed to obtain individual components in a multi-step process. First, the *Stevia* plant is treated to extract an aqueous liquid solution containing mixed sweet glycosides. By using a series of ion exchange resins the impure non-sweet glycosides are separated from the mixed sweet glycosides, which are dried. These dried mixed sweet glycosides, which still contain impurities, are then dissolved in a water-soluble organic solvent such as anhydrous methanol to form a solution. The solution is refluxed and is cooled to precipitate a first sweet glycoside component. This first sweet glycoside component, which is typically Stevioside, can be recovered by filtration and may be further purified by the method described for the second component.

The filtrate from the crystallization of the first precipitated sweet glycoside can be further treated to obtain a second sweet glycoside component by concentrating the filtrate by heating. Upon cooling the solution, a second sweet glycoside component precipitates which can be recovered. This second sweet glycoside component is typically Rebaudioside A. It can be further purified by dissolving it in a water-soluble organic solvent such as methanol that may optionally contain a small amount of water. The solution is heated, refluxed, and finally cooled to precipitate the second sweet glycoside component at a higher purity. The precipitate can be recovered by filtration. This purification process can be repeated until a final crystallized solid of desired purity is obtained. The method reports Rebaudioside A purity levels of 90% or greater or 95% or greater.

U.S. Pat. No. 4,361,697 (Dobberstein et al.) reports a process for recovering diterpene glycosides from the *Stevia rebaudiana* plant. The process includes the steps of sequentially extracting plant material with a first solvent of intermediate polarity to extract plant substances which tend to interfere with a liquid chromatographic separation of the glycosides, and then with a second solvent of high polarity to extract glycosides, and chromatographically separating the extracted glycosides by introducing them onto a liquid chromatography column having a packing of an oxygen-containing organic stationary phase covalently bonded through a silicon atom to an inorganic support. The glycosides are eluted with a solvent of polarity that is higher than that of the first solvent but lower than that of the second solvent.

U.S. Pat. No. 4,892,938 (Giovanetto) reports a method for recovering steviosides from dried plant material of *Stevia rebaudiana* Bertoni by extraction and purification. An extract is obtained through treatment in water at a temperature from room temperature to about 65° C. with stirring and subsequent filtration and centrifugation. This extract is treated with calcium hydroxide, whereupon a precipitate is obtained by means of filtration or centrifugation. This precipitate is treated with a strongly acidic ion exchange resin and subsequently with a weakly basic ion exchange resin, filtered and dried.

U.S. Pat. No. 4,082,858 (DuBois) reports a method for the recovery of rebaudioside A from the leaves of *Stevia rebaudiana* plants. Final purification is achieved by liquid chromatography subsequently followed by an initial extraction with water and alkanol having from 1 to 3 carbon carbons, preferably methanol. It is also disclosed that water may be used as the initial solvent, their preferred solvent at this stage is a liquid haloalkane having from 1 to 4 carbon atoms. The preferred second solvent is an alkanol having from 1 to 3 carbon atoms, while the preferred third solvent is an alkanol having from 1 to 4 carbon atoms and optionally minor amounts of water.

U.S. Patent Application No. 2006/0134292 (Abelyan et al.) reports a process for recovering sweet glycosides from *Stevia rebaudiana* plant material. The dried and powdered leaves are treated with water in the presence of a pectinase, cellulase, and alpha-amylase. The use of such enzymes is reported to considerably increase the extraction rate and facilitates the next stages of purification. The resulting extract is purified using treatment with calcium hydroxide and ultrafiltration. The permeate is passed through the column packed with bentonite and concentrated to syrup state under vacuum. The treatment with ethanol allows separating the practically pure rebaudioside A from the mixture. The rebaudioside A with high purity is obtained after washing the crystals with 88-95% of ethanol.

U.S. Pat. No. 5,972,120 (Kutowy et al.) reports a process for the extraction of sweet compounds from *Stevia rebaudiana Bertoni*, by column extraction, followed by purification by filtration. The extraction is at temperatures in the range of 0° C. to 25° C. Preferably, a pre-treatment step of microfiltration is used to clarify the extract. Purification is by ultrafiltration followed by nanofiltration. The filtration conditions are controlled to optimize the recovery of the sweet compounds.

Other techniques include those reported in Japanese Publication Nos. 56121454; 56121455; 52062300; and 56121453 assigned to Ajinomoto Company, Inc, and in Chinese Publication No. 1243835 assigned to Hailin *Stevia* Rebaudium Sugar.

Improvement in the available techniques and methods for purifying rebaudioside A from *Stevia rebaudiana* ("*Stevia*") is desired. In particular a method that may be conducted at room temperature without the need for heating or cooling steps or energy intensive refluxing is desired.

SUMMARY

The invention provides methods of purifying rebaudioside A from a mixture comprising glycosides of the plant *Stevia rebaudiana* ("*Stevia*"). The methods of the invention are useful for preparing highly pure rebaudioside A compositions from crude *Stevia* starting compositions that are typically considerably lower in rebaudioside A concentration. The highly pure rebaudioside A compositions are useful as non-caloric sweeteners in edible or chewable compositions such as food, beverages, medicine, candy, chewing gum, and the like.

Advantageously, in some embodiments, the method of the invention may be conducted entirely at or near room temperature without the need for energy-intensive refluxing, heating, and/or cooling steps. In addition, the method of the invention does not require chromatographic separations in order to provide high purity rebaudioside A compositions. However, in some embodiments of the invention, the method may comprise one or more of: (i) heating, (ii) cooling, and (iii) chromatographic column separation in order to purify the rebaudioside A composition to achieve a desired level of purity.

In one aspect, the method of the invention comprises the steps of:

(a) providing a *Stevia* starting composition comprising:
rebaudioside A; and
one or more of rebaudioside B, rebaudioside C, rebaudioside D, rebaudioside E, rebaudioside F, stevioside, and dulcoside;

(b) forming a glycoside solution by dissolving the *Stevia* starting composition in a solvent comprising: (i) a mixture of a lower alcohol (e.g., a C1-C3 alcohol) and water, or (ii) a mixture of a lower carboxylic acid (e.g., acetic acid) and water; and (c) adding an antisolvent to the glycoside solution of step (b) in an amount that is effective to cause at least a portion of the rebaudioside A to crystallize from the glycoside solution in the form of a purified rebaudioside A composition having a purity level higher than the *Stevia* starting composition.

In many embodiments, the *Stevia* starting composition comprises about 40% weight or greater rebaudioside A. For example, the *Stevia* starting composition may comprise about 40% to about 80% weight rebaudioside A or about 40% to about 60% weight rebaudioside A.

The *Stevia* starting composition is dissolved in a solvent composition comprising (i) a mixture of a lower alcohol (e.g., a C1 to C3 alcohol) and water; or (ii) a mixture of a lower carboxylic acid (e.g., acetic acid) and water; in order to form a glycoside composition. Examples of useful lower alcohols include methanol, ethanol, and propanol (n-propanol and i-propanol). In many embodiments, the solvent composition comprises a mixture of lower alcohol and water, wherein the lower alcohol portion comprises about 30% to about 70% weight of the solvent composition, and the water portion comprises about 30% to about 70% weight of the solvent composition. In an exemplary embodiment, the solvent composition comprises about 50% weight ethanol and 50% weight water. A solvent composition of a lower carboxylic acid (e.g., acetic acid) and water may also be used. When used as a solvent, the lower carboxylic acid is typically present in an amount ranging from about 30% weight to about 90% weight, and the water is typically present in an amount ranging from about 10% weight to about 70% weight. More typically, the a lower carboxylic acid is present in an amount ranging from about 50% weight to about 90% weight, and the water is present in an amount ranging from about 10% to about 50% weight.

Although any amount below the solubility limit may be used, the *Stevia* starting composition is typically dissolved in the solvent composition to provide a glycoside solution comprising about 15% to about 50% weight of the *Stevia* starting composition and about 50% to about 85% weight of the solvent composition. For example, an exemplary glycoside solution comprises about 30% weight dissolved *Stevia* starting composition and about 70% weight solvent composition, where about 50% of the solvent composition is ethanol and about 50% weight of the solvent composition is water.

After dissolving the *Stevia* starting composition in the solvent composition, an effective amount of an antisolvent is added to the glycoside solution in order to initiate crystallization of the rebaudioside A. The antisolvent functions to change the equilibrium solubility of rebaudioside A in the resulting solution such that the rebaudioside A concentration is supersaturated (i.e., is above its solubility limit). Because the rebaudioside A is above its equilibrium solubility limit, rebaudioside A crystallizes from the solvent composition in the form of purified rebaudioside A crystals.

When a mixture of a lower alcohol (e.g., a C1-C3 alcohol) and water is used as the solvent, the antisolvent typically comprises a lower alcohol, such as a C1-C3 alcohol. Representative examples include methanol, ethanol, propanol (e.g., n-propanol and i-propanol), acetone, and ethyl acetate. The antisolvent may be the same C1-C3 alcohol used in the solvent or it may be a different C1-C3 alcohol. For example, the solvent may comprise ethanol and water, and the antisolvent may comprise methanol. When a lower carboxylic acid and water is used as the solvent, useful antisolvents include methanol, ethanol, propanol (e.g., n-propanol and i-propanol), acetone, and ethyl acetate.

Relative to the mass of the solvent composition, the mass of the antisolvent typically ranges from about 0.5:1 to about 9:1, more typically about 2:1 to about 3:1.

The antisolvent may be added in a single addition (i.e., a single addition of the entire volume of antisolvent) or it may be added in multiple additions, with each providing a fraction of the total required amount of antisolvent. A slower rate of addition, or multiple small additions of the antisolvent may provide a higher purity rebaudioside A composition than if the antisolvent was added in a single addition.

After addition of the antisolvent, the resulting composition is typically stirred at about room temperature in order to allow crystallization of the rebaudioside A to occur. Optionally, the solution may be seeded by the addition of seed crystals comprising very pure rebaudioside A. Typically, crystallization occurs within about 24 hours after the addition of the antisolvent. As a general rule, the time for crystallization decreases as the purity of the rebaudioside A starting composition increases. For example, if the starting composition is relatively pure (e.g., 80% Reb. A) in rebaudioside A, crystallization may take less than 1 hour. In many embodiments, crystallization takes about 1 to 4 hours.

After crystallization, the purified rebaudioside A can be recovered using known techniques such as filtration or centrifugation. After recovery, the purified rebaudioside A crystals can be further purified by washing with a lower alcohol, for example, methanol or ethanol.

In many embodiments, the method of the invention produces purified rebaudioside A compositions that comprise about 90% weight or greater rebaudioside A, for example, about 95% weight or greater rebaudioside A, about 96% weight or greater, about 97% weight or greater, or about 98.5% weight or greater rebaudioside A. In many embodiments, the method of the invention produces purified rebaudioside A compositions that comprise about 2.5% weight or less rebaudioside B, for example, about 2% weight or less rebaudioside B or about 1% weight or less rebaudioside B. In many embodiments, the method of the invention produces purified rebaudioside A compositions that comprises about 1% weight or less rebaudioside D, for example, about 0.5% or less rebaudioside D. The final levels of rebaudioside A, B, and D will typically depend upon the amount of these materials present in the initial feed material.

In yet another aspect, the invention provide a method of washing a solid that comprises rebaudioside A and rebaudioside D in order to remove at least a portion of the rebaudioside D from the solid composition. The method comprising the steps of: (a) providing a solid comprising rebaudioside A and rebaudioside D; and (b) washing the solid with a C1-C3 alcohol to remove at least a portion of the rebaudioside D from the solid composition. Examples of solvents include C1-C3 alcohols such as methanol, ethanol, and propanol. In many embodiments, methanol is preferred for the reduction of rebaudioside D.

DETAILED DESCRIPTION

Figure 1:
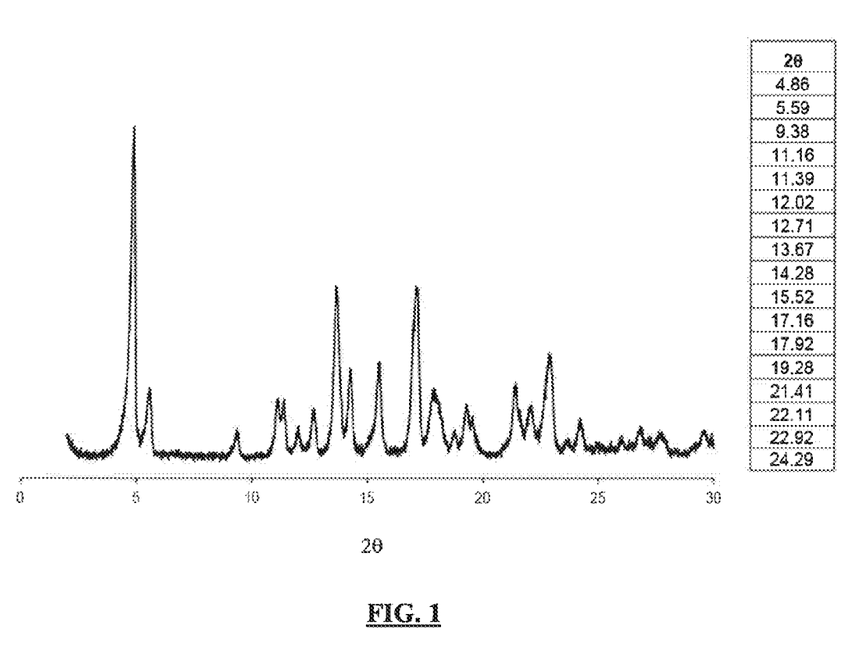
FIG. 1 is an X-ray diffraction pattern for rebaudioside A crystals produced by crystallization from a solvent of ethanol/water using methanol as the antisolvent.
Figure 2:
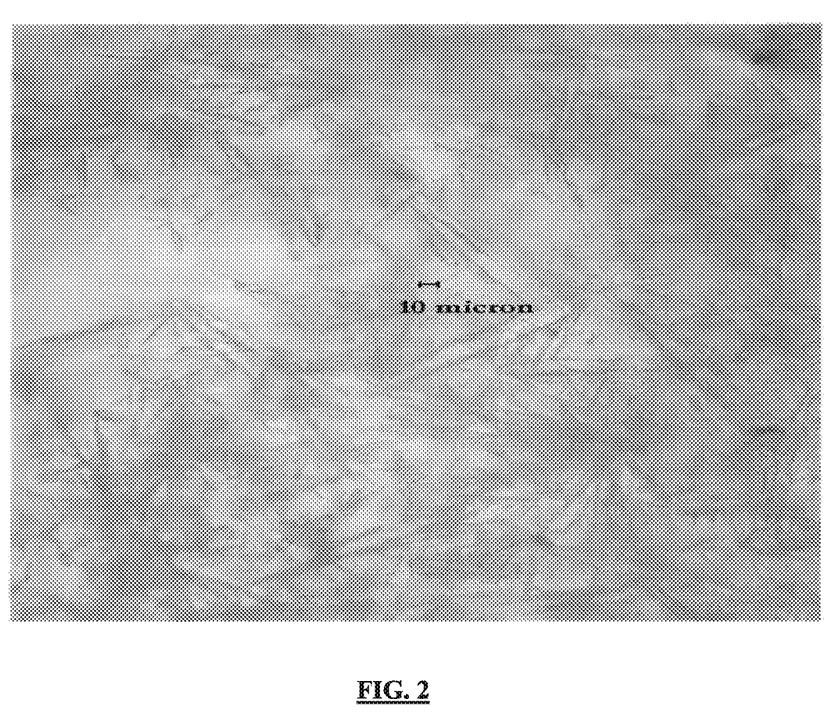
FIG. 2 is a light-microscopy image of rebaudioside A crystals produced by crystallization from a solvent of ethanol/water using methanol as the antisolvent.

In one aspect the invention provides a method of purifying compositions that comprise rebaudioside A. The methods of the invention may be used to prepare highly pure rebaudioside A compositions that are suitable as low-calorie sweeteners in edible or chewable compositions such as food, beverages, medicine, candy, chewing gum, and the like.

In one aspect the invention provides a method of purifying rebaudioside A from a mixture of glycosides. The method comprises the steps of:

(a) providing a *Stevia* starting composition comprising:
   rebaudioside A; and
   one or more of rebaudioside B, rebaudioside C, rebaudioside D, rebaudioside E, rebaudioside F, stevioside, and dulcoside;

(b) forming a glycoside solution by dissolving the glycoside starting composition in a solvent comprising a mixture of: (i) a lower alcohol (e.g., a C1 to C3 alcohol) and water, or (ii) a lower carboxylic acid (e.g., acetic acid) and water; and (c) adding an antisolvent to the glycoside solution of step (b) in an amount that is effective to cause at least a portion of the rebaudioside A to crystallize from the glycoside solution in the form of a purified rebaudioside A composition.

Step (a):

The methods of the invention are useful for purifying starting compositions comprising rebaudioside A in order to form highly pure rebaudioside A compositions. Typically, the starting compositions are derived from the *Stevia rebaudiana* plant using known techniques, such as extraction of diterpene glycosides from *Stevia* leaves using water or solvent-water solutions optionally preceded with a pretreatment, such as extraction of fatty and/or other compounds). Pretreatment operations may include clarification and de-coloration steps (e.g., using coagulants, adsorbents and/or solvent extraction), and may optionally include ash removal by means of ion-exchange. Following this, further purification may be accomplished by selective adsorption, solvent treatment, or a combination. Finally, the starting material may be purified by crystallization and dried. Useful starting compositions comprise rebaudioside A and also comprise one or more other glycosides such as rebaudioside B, rebaudioside C, rebaudioside D, rebaudioside E, rebaudioside F, stevioside, and dulcoside.

In many embodiments the starting compositions comprise about 40% weight or greater rebaudioside A, for example, about 40% to about 95% weight rebaudioside A. Stevioside is also typically present in the staring composition. In some embodiments, stevioside is present up to about 40% weight of the starting composition. Other glycosides that might be present in the starting composition include, for example, rebaudioside B, rebaudioside C, rebaudioside D, and rebaudioside F. Typical starting compositions comprise, for example, up to about 8% weight rebaudioside B, up to about 10% weight rebaudioside C, up to about 2% weight rebaudioside F, up to about 1% weight dulcoside, and up to about 4% weight rebaudioside D. Rebaudioside E may also be present in the starting composition.

Advantageously, the method of the invention may be used to purify rebaudioside A from starting compositions that have a low purity level of rebaudioside A. For example, the method of the invention may be used to produce purified rebaudioside A from starting compositions having less than about 60% weight rebaudioside A, for example, about 40% to about 60% weight rebaudioside A.

Step (b):

In the method of the invention the starting composition is dissolved in a solvent composition in order to form a solution. Typically, the starting composition is added to the solvent composition and the solvent composition is stirred in order to cause the starting composition to dissolve in the solvent composition. The starting composition may be added to the solvent composition at a relatively constant rate over time, or it may be added in one or more discrete additions. Typically, the starting composition is dissolved in the solvent composition at approximately room temperature, for example, about 20° C. to about 25° C. It is also within the scope of the invention to slightly heat the solvent composition somewhat in order to assist with dissolving the starting composition. For example, the solvent composition may be heated to a temperature ranging from about 20° C. to about 70° C., more typically ranging from about 60° C. to about 70° C.

Useful solvent compositions comprise: (i) a mixture of a lower alcohol (e.g., a C1-C3 alcohol) and water; or (ii) a mixture of a lower carboxylic acid and water. Examples of lower alcohols include methanol, ethanol, and propanol (e.g., n-propanol and i-propanol). Mixtures of two or more alcohols and water may also be used. In many embodiments the solvent composition comprises about 20% weight to about 80% weight lower alcohol and about 20% weight to about 80% weight water, based on the total weight of the solvent composition. More typically, the solvent composition comprises about 30% weight to about 70% weight lower alcohol and about 30% weight to about 70% weight water. In exemplary embodiments, the solvent composition comprises about 40% weight to about 60% weight lower alcohol and about 40% weight to about 60% weight water, or about 45% weight to about 55% weight lower alcohol and about 45% weight to about 55% weight water. In an exemplary embodiment, the starting composition comprises about 50% weight ethanol and about 50% weight water.

Examples of lower carboxylic acids include acetic acid, formic acid, and propionic acid although other lower carboxylic acids may also be used. When used as a solvent, the a lower carboxylic acid is typically present in an amount ranging from about 30% weight to about 90% weight, and the water is typically present in an amount ranging from about 10% weight to about 70% weight. More typically, the a lower carboxylic acid is present in an amount ranging from about 50% weight to about 90% weight, and the water is present in an amount ranging from about 10% weight to about 50% weight. In an exemplary embodiment, the solvent composition is 50% weight acetic acid and 50% weight water.

The solvent composition is typically prepared by mixing the individual components together prior to addition of the rebaudioside A starting composition. However, it is also possible to dissolve the rebaudioside A starting composition in one component of the solvent composition and to then add the second component to make up the solvent composition.

Upon dissolving the starting composition in the solvent composition the resulting glycoside solution typically comprises about 15% weight to about 50% weight dissolved solids of the starting composition and about 50% to about 85% weight solvent. In some embodiments, the glycoside solution comprises about 30% weight to about 50% weight dissolved solids and about 50% weight to about 70% weight solvent.

Step (c):

After forming the glycoside solution, an effective amount of an antisolvent is then added to the glycoside solution in order to induce crystallization of rebaudioside A. Upon addition of an effective amount of the antisolvent, the resulting glycoside solution (including the antisolvent) exceeds the solubility limit of rebaudioside A thereby causing rebaudioside A to crystallize from the glycoside solution. Since the other glycosides that may be present in the glycoside solution remain below their solubility limit, rebaudioside A crystallizes preferentially from the solution.

Useful antisolvents include materials that are effective in modifying the solubility limit of rebaudioside A in the glycoside solution. More particularly, an effective antisolvent is both miscible in the glycoside solution and capable of decreasing the solvating power of the water by lowering the dielectric constant of the solution. Typically, the antisolvents are liquids that are water-miscible and are typically less polar than water. Representative examples of antisolvents include lower alcohols (e.g., C1 to C3 alcohols) such as methanol, ethanol, and propanol (n-propanol and i-propanol). Also useful are acetone and ethyl acetate. The antisolvent may be the same lower alcohol that is present in the solvent composition or it may be a different lower alcohol.

In the method of the invention, the antisolvent is added to the glycoside solution in an effective amount to induce crystallization of at least a portion of the rebaudioside A that is present in the glycoside composition. The amount of antisolvent that is needed may depend upon several factors including, for example, the make-up of the solvent composition, the composition of the starting material, the amount of rebaudioside A that is present in the composition, the amount of other glycoside impurities in the solution, crystallization temperature, and dissolution temperature. Typically, the mass of the antisolvent that is added relative to the mass of solvent in the glycoside solution ranges from about 0.5:1 to about 9:1. More typically, the mass of antisolvent relative to the mass of glycoside solution ranges from about 2:1 to about 3:1.

Crystallization of the rebaudioside A may be conducted using either a batch crystallization process or a continuous crystallization process. In a batch process, the starting composition, solvent, and antisolvent are all added to a single container where crystallization occurs. After the crystals are harvested the process can be repeated. In continuous crystallization, a mixture of feed glycosides is dissolved in a solvent solution. The resulting mixture is pumped continuously into a crystallization vessel. At the same time, the antisolvent is pumped into the crystallization vessel in an amount that will result in the desired final antisolvent concentration when mixed with the solvent and solute mixture. Crystallization occurs in this vessel, which is typically at a higher rate than in a batch vessel due to the continual presence of seed crystals. The product slurry is continuously pumped out of the vessel at a rate equal to the sum of the solvent and antisolvent inflows, thus maintaining a constant volume in the crystallizer. The product slurry is filtered or centrifuged, and then dried to provide a final product. Solvents used in the process may be recovered by distillation. Dissolved solute at the end of crystallization can be recovered and either recycled to feed or used separately.

The antisolvent may be added to the glycoside solution in one addition (i.e., the entire amount added in a single addition) or it may be added in multiple additions. In some embodiments, the antisolvent is added to the glycoside solution at a constant rate of addition over time. The rate of addition of the antisolvent to the glycoside solution may affect the purity of the rebaudioside A crystals that are formed. For example, adding the antisolvent in a single addition may cause the rebaudioside A to crystallize rapidly from the glycoside solution resulting in rebaudioside A crystals that are lower in purity than would be formed if the antisolvent was added to the glycoside solution slowly over time, or in multiple small additions.

Typically, the antisolvent is added to the glycoside solution while both materials are maintained at about room temperature, for example, about 20±5° C. After addition of the antisolvent, the resulting glycoside solution is allowed to allowed to stand, with mild to moderate agitation, at approximately room temperature so that the rebaudioside A crystallizes from the glycoside solution. Typically, the rebaudioside A crystallizes within about 24 hours after the addition of the antisolvent. The rate of crystallization typically decreases as the purity of the rebaudioside A starting material decreases.

In some embodiments, the method of the invention further includes the step of cooling the glycoside solution in order to promote crystallization of the rebaudioside A from the glycoside solution. The glycoside solution may be cooled prior to addition of the antisolvent, simultaneous with the addition of the antisolvent, or subsequent to the addition of the antisolvent. Combinations of the foregoing may also be practiced. The glycoside solution may be cooled to any temperature useful to promote crystallization of the rebaudioside A. In some embodiments, the glycoside solution is cooled to a temperature of about 0° C. to about −10° C. The rate of cooling may be any useful rate, but typically ranges from about 1° C./minute to about 5° C./minute.

In some embodiments, the solution is seeded in order to promote crystallization and to enhance purity of the crystallized rebaudioside A. Seeding is typically accomplished by adding a small amount of highly pure rebaudioside A (e.g., about 0.2% to about 10% weight seed loading based on total mass) to the solution.

After crystallization, the purified rebaudioside A can be removed by filtration using well-known techniques and materials. In some embodiments, the purified rebaudioside A crystals are washed using a lower alcohol (e.g., a C1 to C3 alcohol) such as methanol, ethanol, or propanol (n-propanol or i-propanol), or a mixture thereof. Washing with a lower alcohol may be effective in removing residual solvent along with any glycosides that are dissolved in the solvent. Typically, the glycosides that are in the liquid portion of the wet filter cake are lower in rebaudioside A composition than those in the solid part of the wet filter cake. The wash pulls out the glycosides thereby increasing the overall rebaudioside A concentration once the filter cake has dried. In addition, the wash may preferentially remove undesirable glycoside (e.g., remove Reb. B and Reb. D from the Reb. A crystals).

The method of the invention may be used to produce a purified rebaudioside A composition. In some embodiments, the purified rebaudioside A composition comprises about 90% weight or greater rebaudioside A. In other embodiments, the purified rebaudioside A composition comprises about 95% weight or greater rebaudioside A. In yet other embodiments, the purified rebaudioside A composition comprises about 97% weight or greater rebaudioside A. In yet other embodiments, the purified rebaudioside A composition comprises about 98% weight or greater rebaudioside A or about 99% weight or greater rebaudioside A. In many embodiments, the purified rebaudioside A composition comprises about 2.5% weight or less rebaudioside B, or about 2% weight or less rebaudioside B. In many embodiments, the purified rebaudioside A composition comprises about 1% weight or less rebaudioside D, or about 0.5% weight or less rebaudioside D. In many embodiments, the purified rebaudioside A composition comprises about 0.1% weight or less stevioside.

The purified rebaudioside A compositions of the invention can be used as a sole sweetener of food, beverage, medicine, tobacco, pharmaceutical, and personal care products, or mixed with other sweeteners in such products (i.e., as a "co-sweetener"). More than one sweetener is typically used to obtain specific taste profiles and/or physical properties. Such sweeteners include conventional sweeteners (cane sugar, beet sugar, honey, syrups, and other "natural" sweeteners) and high-intensity sweeteners (cyclamates, saccharin, sucralose, aspartame, *Stevia*, and other chemically produced and/or natural high-intensity sweeteners).

In another aspect, the invention provides a method of crystallizing stevioside using solvent/antisolvent crystallization. Crystallization of stevioside from a glycoside composition that comprises rebaudioside A and stevioside may be useful in order to form a purified stevioside composition and also to provide a dissolved glycoside composition that is enriched in rebaudioside A relative to the starting composition. Once enriched in rebaudioside A (e.g., about 20% weight to about 50% weight rebaudioside A), the enriched rebaudioside A composition may be used as a starting material in the above-described process in order to form purified rebaudioside A compositions.

In many embodiments, the method of precipitating stevioside by solvent/antisolvent crystallization comprises the steps of:

(a) providing a glycoside composition comprising rebaudioside A and stevioside (other glycosides are also typically present);

(b) forming a glycoside solution by dissolving the glycoside composition in a solvent comprising a lower alcohol (e.g., a C1 to C3 alcohol and water); and (c) adding an antisolvent to the glycoside solution of step (b) in an amount that is effective to cause at least a portion of the stevioside to crystallize from the glycoside solution thereby forming a glycoside composition that is enriched in rebaudioside A relative to the glycoside solution of step (b).

In some embodiments, the method may further comprise the steps of:

(d) filtering the crystallized stevioside and recovering a composition enriched in rebaudioside A from the glycoside solution of step (c);

(e) forming a second glycoside solution by dissolving the enriched glycoside composition of step (d) in a solvent comprising a lower alcohol (e.g., a C1 to C3 alcohol) and water; and (f) adding an antisolvent to the sweet glycoside solution of step (e) in an amount that is effective to crystallize at least a portion of the rebaudioside A from the sweet glycoside solution in the form of a purified rebaudioside A composition.

The invention will now be described with reference to the following non-limiting examples.

EXAMPLES

Starting Materials

TABLE 1 lists various starting material compositions that were used throughout the Examples.

TABLE 1

| Material | Dulc. (%) | Stev. (%) | Reb. A (%) | Reb. B (%) | Reb. C (%) | Reb. F (%) | Reb. D (%) |
|---|---|---|---|---|---|---|---|
| 59 RA40 | 0.6 | 39.1 | 44.4 | 1.0 | 10.0 | 1.8 | 3.1 |
| 58 RA60 | 0.6 | 29.7 | 56.6 | 1.5 | 7.6 | 1.5 | 2.5 |
| 26 RA80 | 0.2 | 9.3 | 79.2 | 3.6 | 3.4 | 1.0 | 3.2 |
| 70 RA80 | 0.1 | 2.6 | 86.5 | 8.1 | 1.2 | 1.2 | 0.4 |
| RA 20 | 1.6 | 74.1 | 16.0 | 0.0 | 7.0 | 0.7 | 0.6 |

Example 1

First, the starting composition 70 RA80 (see, TABLE 1) was dissolved at 30% weight in a solvent composition comprising 50% weight ethanol and 50% weight water. The resulting solution was allowed to equilibrate overnight at room temperature. Following equilibration the antisolvent methanol was added to the sweet glycoside composition in the amount shown in TABLE 2 in order to provoke crystallization. After the addition of the antisolvent, crystallization was allowed to progress at room temperature overnight. Following crystallization the solutions were filtered and the resulting filter cake was washed with 2 weights of ethanol. The filter cakes and the supernatant samples were then dried and the dried cakes were analyzed by HPLC to determine glycoside composition. The results are reported in TABLE 2.

TABLE 2

| Mat. | Anti-Solvent | Wash | Mass Yield (%) | Reb. A Yield (%) | Dulc. (%) | Stev. (%) | Reb. A (%) | Reb. B (%) | Reb. C (%) | Reb. F (%) | Other (%) |
|---|---|---|---|---|---|---|---|---|---|---|---|
| 70 RA80 | 0.25 wts. MeOH | 2 wts. EtOH | 0.0 | 0.0 | — | — | — | — | — | — | — |
|  |  |  | 0.0 | 0.0 | — | — | — | — | — | — | — |
|  |  |  | 0.0 | 0.0 | — | — | — | — | — | — | — |
| 70 RA80 | 0.50 wts. MeOH | 2 wts. EtOH | 38.1 | 42.0 | 0.0 | 0.2 | 95.5 | 3.9 | 0.1 | 0.2 | 0.2 |
|  |  |  | 0.0 | 0.0 | — | 0.2 | — | — | — | — | — |
|  |  |  | 0.0 | 0.0 | — | 0.2 | — | — | — | — | — |
| 70 RA80 | 1 wts. MeOH | 2 wts. EtOH | 57.7 | 62.7 | 0.0 | 0.0 | 94.1 | 5.1 | 0.0 | 0.3 | 0.1 |
|  |  |  | 57.5 | 63.2 | 0.0 | 0.0 | 95.0 | 4.3 | 0.0 | 0.3 | 0.1 |
|  |  |  | 58.9 | 64.0 | 0.0 | 0.1 | 94.1 | 5.0 | 0.0 | 0.3 | 0.3 |
| 70 RA80 | 2 wts. MeOH | 2 wts. EtOH | 62.0 | 70.2 | 0.0 | 0.2 | 98.0 | 1.5 | 0.0 | 0.2 | 0.4 |
|  |  |  | 62.1 | 70.4 | 0.0 | 0.1 | 98.1 | 1.4 | 0.0 | 0.1 | 0.4 |
|  |  |  | 62.2 | 70.6 | 0.0 | 0.0 | 98.3 | 1.1 | 0.0 | 0.2 | 0.3 |
| 70 RA80 | 3 wts, MeOH | 2 wts. EtOH | 65.6 | 73.5 | 0.0 | 0.0 | 96.9 | 2.3 | 0.0 | 0.2 | 0.4 |
|  |  |  | 64.1 | 72.2 | 0.0 | 0.0 | 97.4 | 1.9 | 0.0 | 0.2 | 0.4 |
|  |  |  | 64.7 | 73.2 | 0.0 | 0.0 | 97.9 | 1.6 | 0.0 | 0.2 | 0.4 |
| 70 RA80 | 4 wts. MeOH | 2 wts. EtOH | 64.2 | 72.2 | 0.0 | 0.0 | 97.3 | 2.1 | 0.0 | 0.2 | 0.4 |
|  |  |  | 64.5 | 72.7 | 0.0 | 0.0 | 97.5 | 1.9 | 0.0 | 0.2 | 0.4 |
|  |  |  | 60.8 | 68.4 | 0.0 | 0.0 | 97.4 | 2.0 | 0.0 | 0.2 | 0.4 |

* Other = sum of peaks between Reb. A and Reb. B, which is believed to include Reb. D and Steviolbioside.

Example 2

First, the starting materials identified in TABLE 3 were dissolved at 30% weight in a solvent composition comprising 50% weight ethanol and 50% weight water. The resulting solutions were allowed to equilibrate overnight at room temperature. Following equilibration, 2 volumes of antisolvent were added to the sweet glycoside composition to provoke crystallization. After the addition of the antisolvent, crystallization was allowed to progress at room temperature overnight. The addition of 2 volumes of antisolvent was observed to cause crystallization in the 80% Reb. A starting materials but did not result in crystallization in the sweet glycoside compositions prepared from 60% or 40% Reb. A starting compositions. An additional volume of antisolvent was added to the glycoside compositions prepared from 60% and 40% Reb. A starting compositions. The additional volume of ethanol antisolvent caused crystallization to occur in two of the three samples prepared with 60% Reb. A. The additional volume of ethanol antisolvent did not cause crystallization to occur in any of the samples prepared with 40% Reb. A. The additional volume of methanol antisolvent caused crystallization to occur in all three samples prepared with 40% Reb. A and in all three samples prepared with 60% Reb. A. Following crystallization the solutions were filtered and the resulting filter cake were washed with 2 volumes of ethanol. The filter cakes were then dried and the dried cakes were analyzed by HPLC to determine glycoside composition. The results are reported in TABLE 3.

TABLE 3

| Mat. | Anti-solvent | Wash | Mass Yield | Reb. A Yield | Dulc. | Stev. | Reb. A | Reb. B | Reb. C | Reb. F | Other |
|---|---|---|---|---|---|---|---|---|---|---|---|
| 70 RA80 | 2 wts EtOH | 2 wts EtOH | 50.1 | 55.8 | 0.1 | 0.0 | 98.3 | 1.4 | 0.0 | 0.2 | 0.0 |
|  |  |  | 46.0 | 51.3 | 0.1 | 0.0 | 98.4 | 1.4 | 0.0 | 0.1 | 0.0 |
|  |  |  | 46.9 | 52.6 | 0.1 | 0.0 | 98.9 | 1.0 | 0.0 | 0.1 | 0.0 |
| 70 RA80 | 2 wts MeOH | 2 wts EtOH | 38.1 | 42.0 | 0.1 | 0.0 | 97.6 | 1.8 | 0.0 | 0.2 | 0.3 |
|  |  |  | — | — | 0.1 | 0.0 | 97.7 | 1.8 | 0.1 | 0.2 | 0.1 |
|  |  |  | — | — | 0.3 | 0.0 | 97.6 | 1.8 | 0.1 | 0.2 | 0.0 |
| 70 RA60 | 3 wts EtOH | 2 wts EtOH | 57.7 | 62.7 | 0.4 | 0.0 | 95.5 | 2.9 | 0.1 | 0.2 | 0.8 |
|  |  |  | 57.5 | 63.2 | 0.3 | 0.0 | 96.1 | 2.6 | 0.1 | 0.3 | 0.6 |
|  |  |  | 58.9 | 64.0 | — | — | — | — | — | — | — |
| 70 | 3 wts | 2 wts | 62.0 | 70.2 | 0.2 | 0.0 | 97.5 | 1.4 | 0.1 | 0.3 | 0.4 |

TABLE 3-continued

| Mat. | Anti-solvent | Wash | Mass Yield | Reb. A Yield | Dulc. | Stev. | Reb. A | Reb. B | Reb. C | Reb. F | Other |
|---|---|---|---|---|---|---|---|---|---|---|---|
| RA60 | MeOH | EtOH | 62.1 | 70.4 | 0.3 | 0.0 | 97.8 | 1.1 | 0.2 | 0.3 | 0.3 |
|  |  |  | 62.2 | 70.6 | 0.4 | 0.0 | 97.8 | 0.9 | 0.2 | 0.3 | 0.3 |
| 70 RA40 | 3 wts EtOH |  | 65.6 | 73.5 | — | — | — | — | — | — | — |
|  |  |  | 64.1 | 72.2 | — | — | — | — | — | — | — |
|  |  |  | 64.7 | 73.2 | — | — | — | — | — | — | — |
| 70 RA40 | 3 wts MeOH | 2 vol. EtOH | 64.2 | 72.2 | 0.3 | 0.0 | 98.1 | 0.6 | 0.2 | 0.4 | 0.4 |
|  |  |  | 64.5 | 72.7 | 0.2 | 0.0 | 98.2 | 0.6 | 0.2 | 0.5 | 0.3 |
|  |  |  | 60.8 | 68.4 | 0.6 | 0.0 | 97.6 | 0.6 | 0.3 | 0.4 | 0.4 |

* Other = sum of peaks between Reb. A and Reb. B which is believed to include Reb. D and Steviolbioside.

Example 3

RA 20 (see, TABLE 1) was dissolved in a solution of 50% ethanol and 50% water to produce a solution containing 30% by weight RA 20. The solution was diluted with 3 weights of methanol, filtered, and washed with two weights of methanol. The crystals constituted 56% by weight of the original material, and were enriched in Stevioside. The filtrate constituted the balance of the material, and was enriched in Reb. A. The purity of the resulting crystals and filtrate are provided in TABLE 4.

TABLE 4

|  | Dulc | Stev | Reb. A | Reb. B | Reb. C | Reb. F | Other* |
|---|---|---|---|---|---|---|---|
| Crystals | 0.0% | 93.2% | 3.9% | 0.1% | 0.5% | 0.0% | 2.2% |
| Filtrate | 0.0% | 29.8% | 40.8% | 60.0% | 21.9% | 4.1% | 2.8% |

*Other = sum of peaks between Reb. A and Reb. B which is believed to include Reb. D and Steviolbioside.

Example 4

A raw material of steviol glycosides containing about 60% by weight Reb A was dissolved in a solvent containing 65% by weight ethanol and 35% by weight water to produce a solution containing 56% by weight steviol glycosides. The solution was heated to about 70° C. such at which point all the glycosides were dissolved. 100% ethanol was added as an antisolvent such that the final composition of the solvent was 89.3% ethanol by weight. Simultaneously with the addition of ethanol, the solution was cooled slowly over about 2 hours to room temperature. The resulting crystals were filtered from the solution and washed with 2 cake weights of 95% ethanol, and was dried. The filter cake contained 95-97% RebA by weight on a dry basis. About 75% of the Rebaudioside A in the solution was recovered in the crystallization.

Example 5

A raw material of steviol glycosides containing about 80% by weight Reb A was dissolved in a solvent containing 85% by weight ethanol and 15% by weight water to produce a solution containing 15% by weight steviol glycosides. The solution was heated to about 70° C. such at which point all the glycosides were dissolved. 100% ethanol was added as an antisolvent such that the final composition of the solvent was 89.3% ethanol by weight. Simultaneously with the addition of ethanol, the solution was cooled slowly over about 2 hours to room temperature. The resulting crystals were filtered from the solution and washed with 2 cake weights of 95% ethanol, and was dried. The filter cake contained 94-95% RebA by weight on a dry basis. Greater than 95% of the Rebaudioside A in the solution was recovered in the crystallization.

Other embodiments of this invention will be apparent to those skilled in the art upon consideration of this specification or from practice of the invention disclosed herein. Variations on the embodiments described herein will become apparent to those of skill in the relevant arts upon reading this description. The inventors expect those of skill to use such variations as appropriate, and intend to the invention to be practiced otherwise than specifically described herein. Accordingly, the invention includes all modifications and equivalents of the subject matter recited in the claims as permitted by applicable law. All patents, patent documents, and publications cited herein are hereby incorporated by reference as if individually incorporated.

What is claimed is:

1. A method of purifying rebaudioside A from a mixture of glycosides, the method comprising the steps of:
   (a) providing a glycoside starting composition comprising: about 40-80 wt % rebaudioside A; and one or more of rebaudioside B, rebaudioside C, rebaudioside D, rebaudioside E, rebaudioside F, stevioside, and dulcoside;
   (b) forming a glycoside solution by dissolving the glycoside starting composition in a solvent comprising; a mixture of a lower alcohol and water, and
   (c) adding an antisolvent to the glycoside solution of step (b) in an amount that is effective to cause at least a portion of the rebaudioside A to crystallize from the glycoside solution in a single crystallization step having a purity of about 90-99 wt % rebaudioside A with a yield of about 60-95 wt % wherein the added antisolvent is different than the lower alcohol and water.

2. The method of claim 1, wherein the method further includes the step of seeding the glycoside solution of step (c) by adding crystals comprising rebaudioside A to the glycoside solution.

3. The method of claim 1, wherein the method is conducted as a batch crystallization process.

4. The method of claim 1, wherein the method is conducted as a continuous crystallization process.

5. The method of claim 1, wherein the glycoside starting composition comprises about 60% weight or less rebaudioside A.

6. The method of claim 1, wherein the glycoside starting composition comprises about 40% to about 60% weight rebaudioside A.

7. The method of claim 1, wherein the lower alcohol comprises a C1 to C3 alcohol.

8. The method of claim 7, wherein the C1 to C3 alcohol is selected from methanol, ethanol, n-propanol, i-propanol, or a mixture thereof.

9. The method of claim 7, wherein the C1 to C3 alcohol is ethanol.

10. The method of claim 1, wherein the solvent comprises about 30% to about 70% weight C1 to C3 alcohol and about 30% to about 70% weight water.

11. The method of claim 1, wherein solvent comprises about 40% to about 60% weight C1 to C3 alcohol and about 40% to about 60% weight water.

12. The method of claim 1, wherein the solvent comprises about 45% to about 55% weight C1 to C3 alcohol and about 45% to about 55% weight water.

13. The method of claim 1, wherein the antisolvent comprises a C1 to C3 alcohol, or a mixture thereof.

14. The method of claim 1, wherein the antisolvent comprises methanol, ethanol, i-propanol, n-propanol, acetone, ethyl acetate, or a mixture thereof.

15. The method of claim 1, wherein the solvent comprises ethanol and water; and wherein the antisolvent comprises ethanol.

16. The method of claim 1, wherein the solvent comprises ethanol and water; and wherein the antisolvent comprises methanol.

17. The method of claim 1, wherein the mass of antisolvent relative to the mass of the glycoside solution ranges from about 0.50:1 to about 9:1.

18. The method of claim 1, wherein the mass of the antisolvent relative to the mass of the glycoside solution ranges from about 1:1 to 3:1.

19. The method of claim 1, wherein the glycoside solution comprises about 15% weight to about 50% weight starting composition; and about 50% to about 85% weight solvent.

20. The method of claim 1, further including the step of recovering the purified rebaudioside A composition by filtration.

21. The method of claim 1, further including the step of washing the purified rebaudioside A composition with a C1 to C3 alcohol, or a mixture thereof.

22. The method of claim 21, wherein the alcohol is ethanol.

23. The method of claim 21, wherein the alcohol is methanol.

24. The method of claim 1, wherein the purified rebaudioside A composition comprises about 90% weight or greater rebaudioside A.

25. The method of claim 1, wherein the purified rebaudioside A composition comprises about 95% weight or greater rebaudioside A.

26. The method of claim 1, wherein the purified rebaudioside A composition comprises about 97% weight or greater rebaudioside A.

27. The method of claim 1, wherein the purified rebaudioside A composition comprises about 98% weight or greater rebaudioside A.

28. The method of claim 1, wherein the purified rebaudioside A composition comprises about 2.5% weight or less rebaudioside B.

29. The method of claim 1, wherein the purified rebaudioside A composition comprises about 2% weight or less rebaudioside B.

30. The method of claim 1, wherein the purified rebaudioside A composition comprises about 1% weight or less rebaudioside D.

31. The method of claim 1, wherein the purified rebaudioside A composition comprises about 0.5% weight or less rebaudioside D.

32. The method of claim 1, wherein the antisolvent is added in a single addition to the glycoside solution.

33. The method of claim 1, wherein the antisolvent is added to the glycoside solution in multiple additions.

34. The method of claim 1, wherein the antisolvent is added to the glycoside solution continuously.

35. The method of claim 1, wherein the glycoside solution and the antisolvent are at a temperature ranging from about 15° C. to about 25° C.

36. The method of claim 1, wherein the step of forming the glycoside solution includes heating the solvent to a temperature ranging from about 60° C. to about 70° C.

37. The method of claim 1, wherein the method further includes the step of cooling the glycoside solution.

38. The method of claim 37, wherein the step of cooling the glycoside solution occurs: (i) before the addition of the antisolvent; (ii) simultaneously with the addition of the antisolvent; (iii) after the addition of the antisolvent; or any combination thereof.

39. The method of claim 37, wherein the glycoside solution is cooled to a temperature ranging from about 0° C. to about −10° C.

40. The method of claim 37, wherein the glycoside solution is cooled at a rate ranging from about 1° C./minute to about 5° C./minute.

41. A method of purifying rebaudioside A from a mixture of glycosides, the method comprising the steps of:
(a) providing a glycoside starting composition comprising about 40-80 wt % rebaudioside A; and one or more of rebaudioside B, rebaudioside C, rebaudioside D, rebaudioside E, rebaudioside F, stevioside, and dulcoside;
(b) forming a glycoside solution by dissolving the glycoside starting composition in a solvent comprising ethanol and water; and
(c) adding an antisolvent of ethanol or methanol to the glycoside solution of step (b) in an amount that is effective to cause rebaudioside A to crystallize from the solution in a single crystallization step having a purity of about 90-99 wt % rebaudioside A with a yield of about 60-95 wt %.

42. The method of claim 41, wherein the antisolvent is ethanol.

43. The method of claim 41 wherein the glycoside starting composition comprises about 40 wt % rebaudioside A and the single crystallization step provides about 97-99 wt % rebaudioside A with a yield of about 60-75 wt %.

44. The method of claim 41 wherein the glycoside starting composition comprises about 60 wt % rebaudioside A and the single crystallization step provides about 97-99 wt % rebaudioside A with a yield of about 70-75 wt %.

45. The method of claim 41 wherein the glycoside starting composition comprises about 80 wt % rebaudioside A and the single crystallization step provides about 94-99 wt % rebaudioside A with a yield of about 60-75 wt %.

* * * * *